United States Patent [19]

Tierney et al.

[11] Patent Number: 5,304,293

[45] Date of Patent: Apr. 19, 1994

[54] MICROSENSORS FOR GASEOUS AND VAPOROUS SPECIES

[75] Inventors: Michael J. Tierney; Arvind Jina, both of Redwood City; Jose Joseph, Menlo Park; Marc Madou, Palo Alto, all of Calif.

[73] Assignee: Teknekron Sensor Development Corporation, Menlo Park, Calif.

[21] Appl. No.: 882,459

[22] Filed: May 11, 1992

[51] Int. Cl.⁵ .................................. G01N 27/26
[52] U.S. Cl. .................................. 204/414; 204/415; 204/431; 204/432; 204/424
[58] Field of Search ............... 204/415, 414, 412, 418, 204/403, 424, 425, 426, 427, 428, 429, 431, 432, 283

[56] References Cited

U.S. PATENT DOCUMENTS

| | | | |
|---|---|---|---|
| 4,457,822 | 7/1984 | Asano et al. | 204/283 |
| 4,671,288 | 6/1987 | Gough | 204/415 |
| 4,703,756 | 11/1987 | Gough et al. | 204/415 |
| 4,781,798 | 11/1988 | Gough | 204/415 |
| 4,812,221 | 3/1989 | Madou et al. | 204/415 |
| 4,890,620 | 1/1990 | Gough | 204/415 |
| 4,900,405 | 2/1990 | Otagawa et al. | 204/412 |

*Primary Examiner*—John Niebling
*Assistant Examiner*—Bruce F. Bell
*Attorney, Agent, or Firm*—Limbach & Limbach

[57] ABSTRACT

A sensor for gaseous and vaporous species is disclosed. The sensor comprises an electrically insulated substrate which contains small pores passing completely through it. Electrodes consisting of metallic or semiconductor material are deposited onto the top surface of the substrate. In a first embodiment of the invention, an electrolyte is placed on the top surface of the substrate in such a manner as to create a gas or vapor permeable electrolyte layer on top of the electrodes. In a second embodiment of the invention, the electrolyte is applied to the bottom surface of the substrate and seeps up through the porous holes of the substrate until it makes contact with the electrodes. Both embodiments result in a gas sensor with a response time dependent upon the gas flow rate rather than the time required for the gas to be dissolved in the electrolyte layer and be detected.

18 Claims, 4 Drawing Sheets

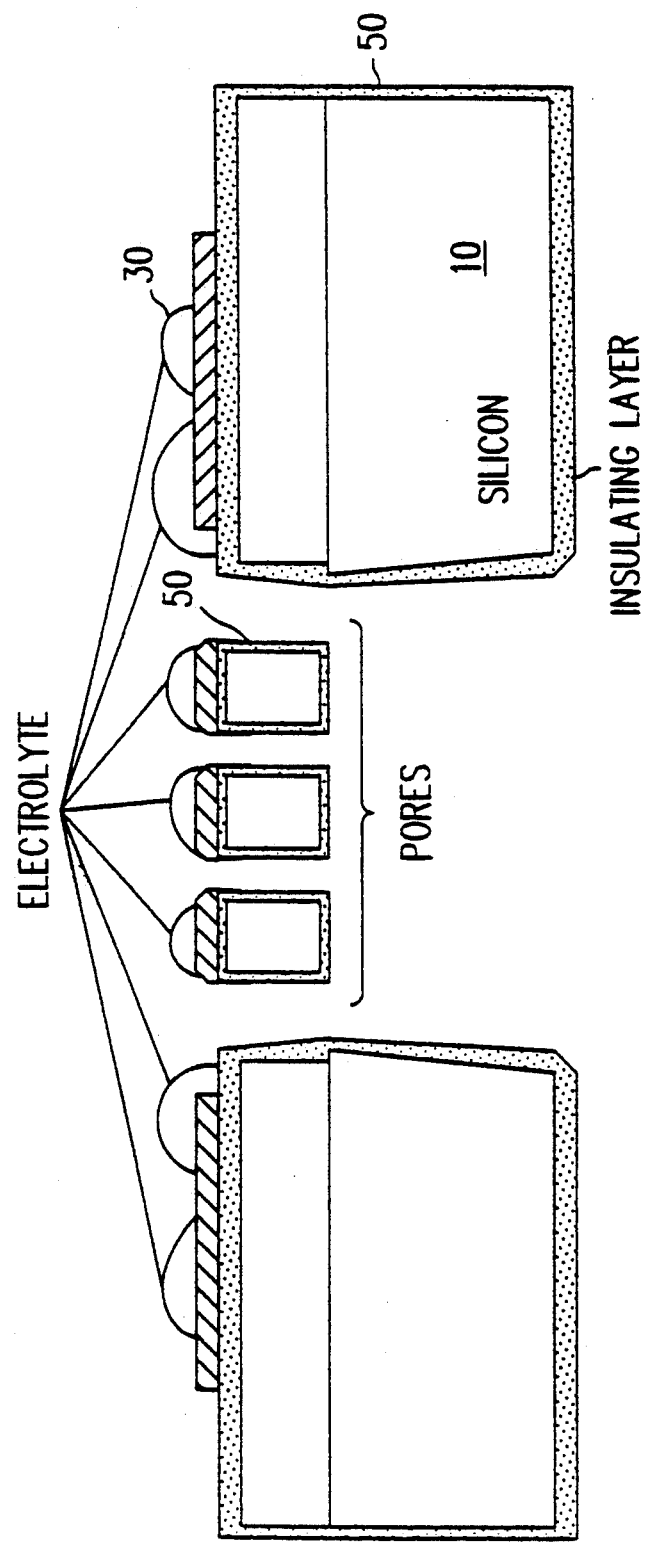

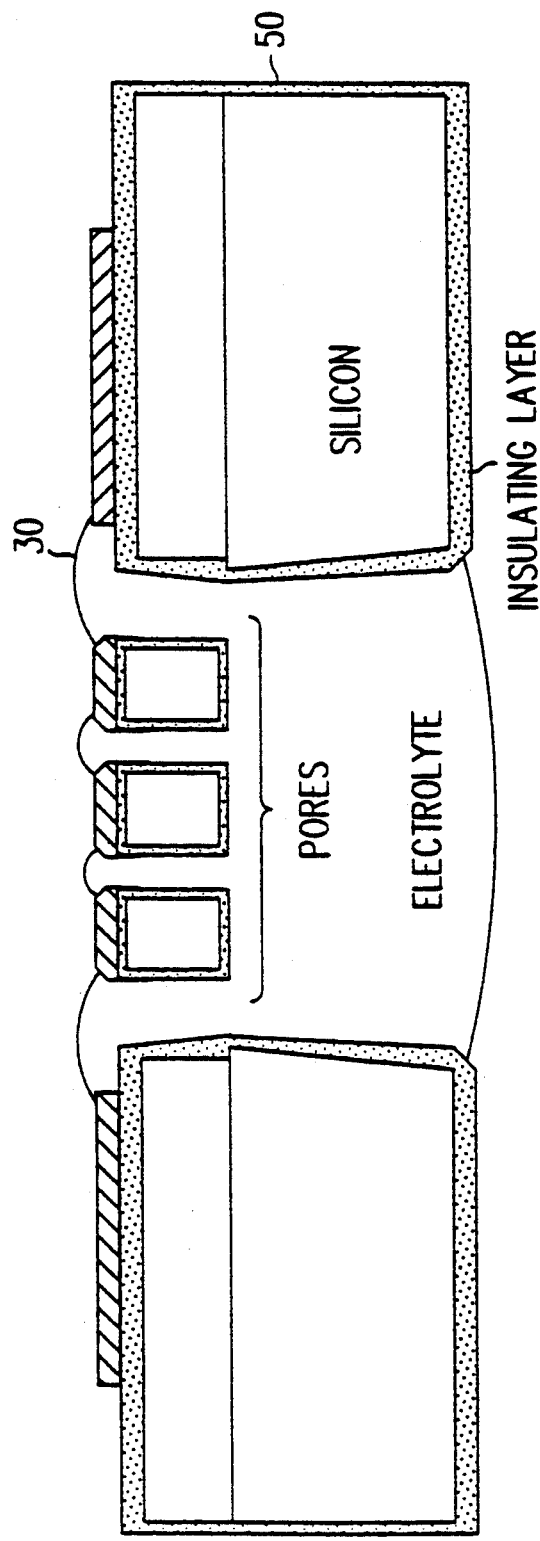

MICROSENSORS FOR GASEOUS AND VAPOROUS SPECIES

TECHNICAL FIELD

The subject invention relates to a microsensor for detecting gaseous and vaporous species.

BACKGROUND OF THE INVENTION

Microsensors are utilized to detect a variety of gaseous and vaporous species in circumstances where the physical size of the sensor is a constraint. Such uses can include detection of species within the human body, such as monitoring the glucose level in patients afflicted with diabetes mellitus by sensing the concentration of oxygen in their blood. Other uses include in vivo or in vitro blood gas sensing, monitoring gas concentrations in closed-loop life support systems, and anesthetic gas monitoring.

One type of sensor currently in use is a so-called planar Clark-type sensor. In such sensors a sensing electrode and a reference electrode are deposited on a substrate using conventional semiconductor fabrication techniques. A hydrogel layer is then deposited on the substrate and serves as the electrolytic medium in which the species to be detected dissolves, facilitating its detection by the sensing electrode.

Madou et al. in U.S. Pat. No. 4,812,221 discloses a sensor for gaseous and vaporous species which comprises a substrate with passages connecting the top and bottom surfaces of the substrate, and through which gas can flow from one surface of the substrate to the other. A gas and vapor permeable sensing electrode is positioned adjacent to the passages. An electrolytic medium is then placed in contact with the top surfaces of the electrode and the substrate. Means for encapsulating the electrode and the electrolyte can be utilized, if desired, to seal the components into one unit and maintain the operational characteristics of the sensor over time.

The above steps provide a microsensor whose active detecting region is limited to that part of the gas permeable electrode which is in contact with the substrate passages or can be reached through diffusion by the gaseous species. This affects its response time and sensitivity because the species must pass through the passages and come into contact with the electrode and electrolytic medium in order to be detected. The number of points at which the gas, electrode, and electrolyte meet determines the amount of interactions necessary to generate a detection (sensitivity).

It is therefore desirable to have a microsensor having faster response time and a higher sensitivity owing to a more distributed active sensing region, so that gaseous or vaporous species can be detected and analyzed within the timescale necessary for their use in time-constrained applications.

SUMMARY OF THE INVENTION

In accordance with this objective, the subject invention provides a microsensor for gaseous and vaporous species. Two embodiments of the invention are disclosed. Both embodiments have a common substrate which consists of an electrically insulating material or one which has an insulating surface coating. The substrate is manufactured so as to contain small pores passing through its thickness. Electrodes consisting of a metallic or semiconducting material are then deposited onto one face of the sensor substrate.

In a first embodiment of the invention an electrolytic substance is placed on the sensor surface which contains the electrodes. The electrolyte is prepared by forming a solution of the desired electrolytic substance dissolved in an appropriate solvent. The substrate surface is first heated to a temperature near the boiling point of the solvent used in the electrolytic solution. The subsequent application of the electrolytic solution to the heated surface causes the solvent to evaporate, forming holes in the electrolyte layer coating the electrodes.

In a second embodiment of the invention an electrolyte gel is placed in contact with the surface of the sensor substrate which does not contain the electrodes (the backside). The gel is allowed to flow through the pores of the substrate until it comes in contact with the surface containing the electrodes, and the electrodes themselves. If desired, a mass of gel on the back side can serve as a reservoir and act to maintain the operability of the sensor over an extended period of time.

Further objects and advantages of the subject invention will become apparent from the following detailed description and the accompanying drawings.

BRIEF DESCRIPTION OF THE DRAWINGS

FIG. 4 is a side view of another embodiment of a microsensor of the present invention which is substantially similar to that of the embodiment of FIG. 1 and includes an electrically insulating coating around the substrate regions which are separated by pores, thus insulating those regions from the electrodes.

FIG. 5 is a side view of another embodiment of a microsensor of the present invention which is substantially similar to that of the embodiment of FIG. 3 and includes an electrically insulating coating around the substrate regions which are separated by pores, thus insulating those regions from the electrodes.

DESCRIPTION OF THE PREFERRED EMBODIMENT

Figure 1:
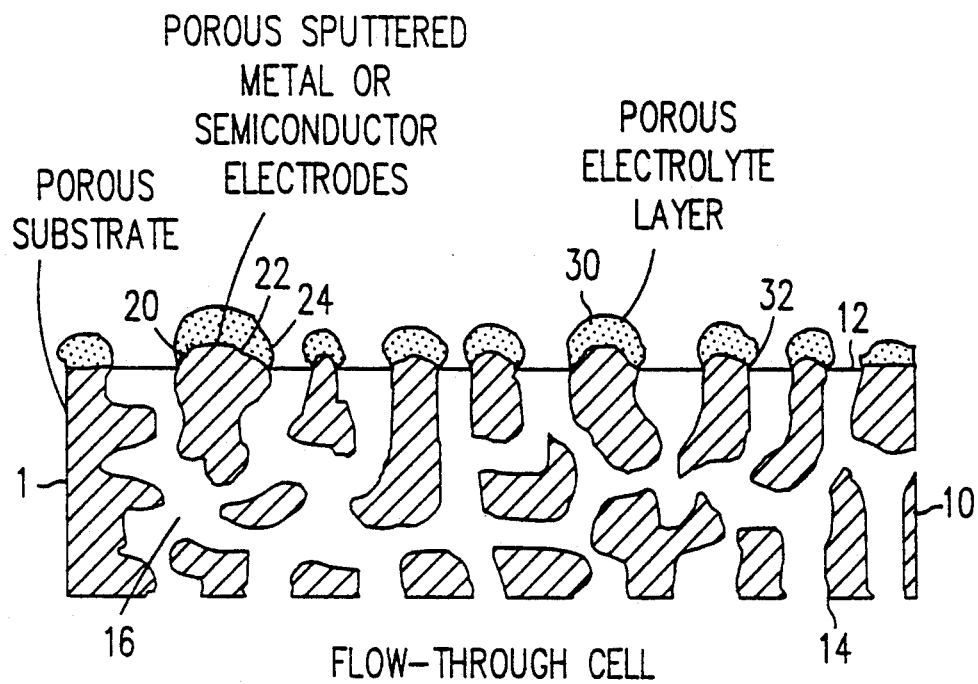
FIG. 1 is a side view of one embodiment of a microsensor of the present invention.

Referring to FIG. 1, there is illustrated one embodiment of a microsensor 1 of the present invention. The sensor cell 1 consists of a substrate 10, having a top surface 12 and a bottom surface 14. The surfaces 12 and 14 are generally opposed to one another. Substrate 10 is a thin material on the order of 1 mm which is electrically insulating. Examples of suitable materials include porous ceramics, sintered glass, or porous plastic.

Electrodes 20 with a top surface 22 and a bottom surface 24 are placed on the top surface 12 of the substrate 10. The sensors may be constructed with either two or three electrodes. Two electrode sensors are used for potentiometric and conductimetric sensing, and may be used for amperometric sensing. Three electrode sensors are used only for amperometric sensing. A porous electrolyte layer 30 is placed on the top surface 22 of the electrodes 20 by a method described later in this specification.

The substrate 10 is prepared so that it contains small (less than 50 microns diameter) pores 16 passing through its thickness from the bottom surface 14 to the top surface 12. The pores 16 can be made to run parallel to each other directly through the substrate 10. This can be accomplished, for example, by electrochemically oxidizing an aluminum film in an acidic bath to form an aluminum oxide membrane with parallel pores running through its thickness.

Alternately, the substrate 10 can consist of a microporous material such as porous ceramic or sintered glass wherein the pores 16 have tortuous paths. Tortuous path substrates may be formed by sintering ceramic, glass, or plastic particles, or particles of other appropriate materials. The pores 16 serve to allow the species to be detected to enter and flow through the sensor cell 1 to come in contact with the electrodes 20, and electrolyte layer 30.

The electrodes 20 are deposited onto the top surface 12 of the substrate 10 by known methods, such as, for example, evaporation, sputtering, and screen printing. The electrodes may consist of electrically conducting materials such as platinum, gold, carbon, silver, iridium oxide, tin oxide, silicon, or any of the organic conducting compounds. The deposition process results in the electrodes 20 themselves being porous and therefore gas and vapor permeable.

The electrolyte layer 30 is composed of a hydrogel, or a polymer electrolyte such as Nafion (a trademark of DuPont). To form the electrolyte layer 30 a solution of the electrolyte and a suitable solvent is prepared. Examples of suitable solvents are water, methanol, ethanol, and glycerol. Additional electrolyte species, such as potassium chloride, sodium chloride, sodium bicarbonate, or any other electrolyte species, may be added to the solution. The resulting concentration of the electrolyte should be in a range to allow optimum sensor operation. For example, most amperometric mode sensors operate well with electrolyte concentrations of 0.1M. Similarly, potentiometric carbon dioxide sensors display highest sensitivity with a bicarbonate concentration of $10^{-2}$–$10^{-4}$M.

Prior to application of the electrolyte solution, the substrate 10 is heated to a temperature near the boiling point of the chosen solvent. Then the electrolyte solution is placed onto the top surface 12 of the substrate 10. The electrolyte solution is also placed on the top surface 22 of the electrodes 20. The solvent of the solution evaporates quickly, forming holes in the electrolyte layer which pass from the top surface of the electrodes 22 through the electrolyte layer 30 to the top surface of the electrolyte. The result is a porous electrolyte layer 30 covering the electrodes 20.

An alternate method of forming a porous electrolyte layer 30 is to place the electrolyte solution on the substrate 10 which contains pores 16 so large that the resulting electrolyte film does not completely close the pores. Either method results in a sensor substrate 10 on one surface of which is a set of porous electrodes 20 covered with a porous electrolyte layer 30. This results in a cell 1 having a fast response time because the gaseous or vaporous species can contact the gas-electrode-electrolyte "triple points" 32 directly, without the necessity of first diffusing through the electrolyte layer 30. The electrolyte layer 30, however, is necessary for the detection of the species by providing one of the required reactants for the chemical reaction and/or providing an electrolytic medium to complete the electrochemical sensing circuit. Typical sensing reactions may include electrochemical oxidation or reduction of the gas in the case of amperometric-mode operation, or sensing of a change in the properties of the electrolyte (for example, pH) for potentiometric-mode sensing. The microsensor 1 is superior to that disclosed in Madou et al. because of its inherent features of a larger active sensing area and faster response time.

The faster response time of this Flow-through cell embodiment of the microsensor 1 of the present invention results because the gas or vapor can move through the sensor from the substrate backside 14 through the pores 16, and thus its concentration reaches an equilibrium value at the electrode 20 more quickly. It is important to achieve an equilibrium concentration value because this is when the signal from the sensor becomes steady. The signal is an electrical current resulting from a reaction of the gas or vapor at the electrode within the electrolyte in the case of amperometric-mode operation, or an electrical voltage or potential resulting from a change in the concentration of a reaction product or reactant at the electrode in the case of potentiometric-mode operation. The electrolyte does not necessarily participate in the reaction (although it may), but provides a medium in which the reaction can take place, and through which it can be detected.

The sensor 1 response time is thus a function of the species flow rate through the substrate 10 and diffusion rate through the porous electrolyte layer 30, rather than its diffusion rate within a nonporous electrolyte layer. The sensor contains a multitude of potential gas-electrode-electrolyte "triple points" 32 where the gaseous species, the porous electrode 20, and the porous electrolyte layer 30 come in contact, so that its detection ability (response time and sensitivity) is enhanced.

Figure 2:
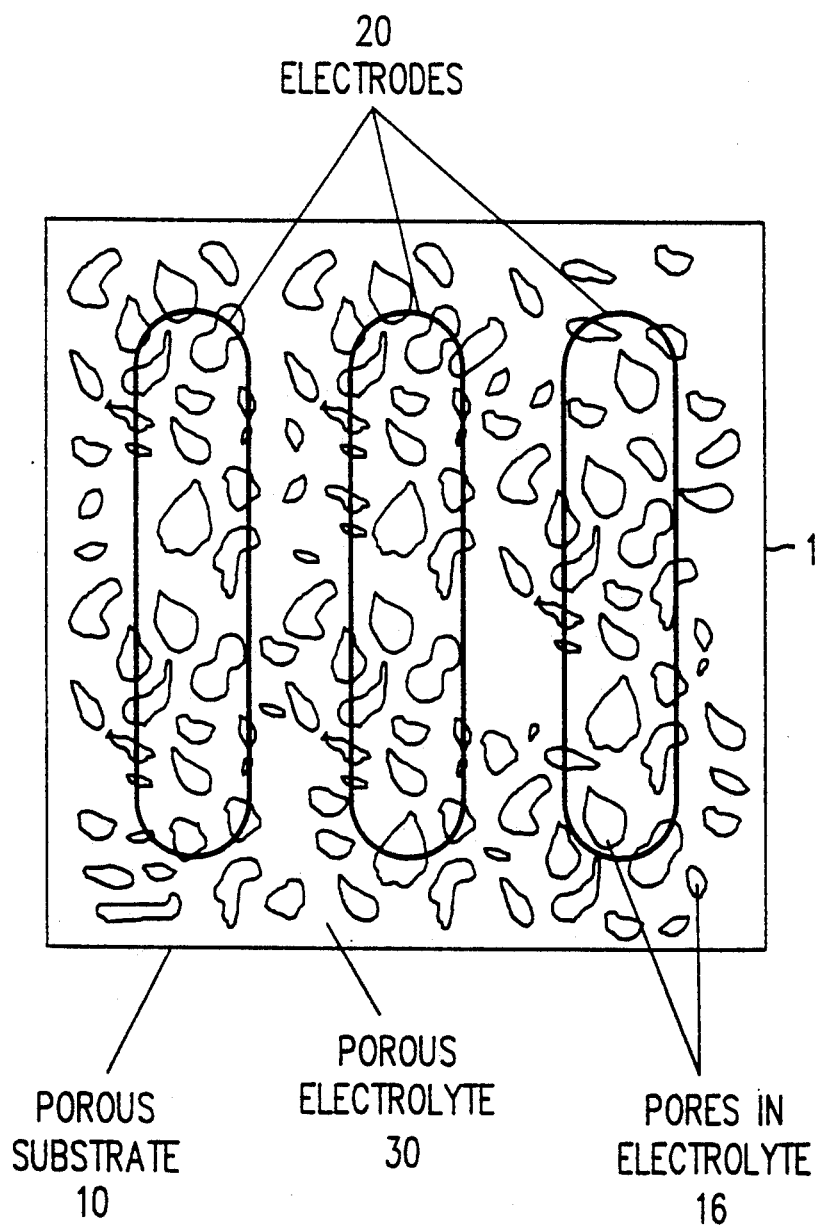
FIG. 2 is a top view of the Flow-through microsensor shown in FIG. 1.

Referring to FIG. 2, there is shown a top view of the Flow-through cell embodiment of the microsensor 1 of the present invention. This figure depicts the substrate 10, the electrodes 20, the porous electrolyte layer 30, and the pores 16 in the electrolyte. The pores 16 in the electrolyte layer 30 are shown proportionately larger in the figure than they are in actuality.

Figure 3:
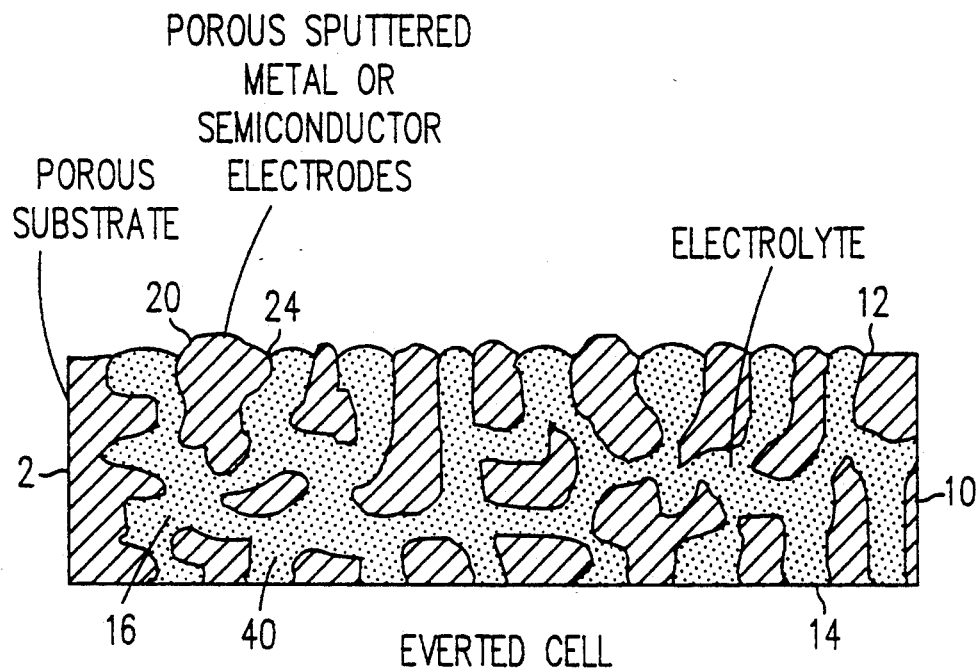
FIG. 3 is a side view of another embodiment of a microsensor of the present invention.

Referring to FIG. 3, there is shown a second embodiment of a microsensor 2 of the present invention. As in the previously described embodiment, the sensor 2 is composed of a substrate 10 which has been manufactured so as to have pores 16, and on whose top surface 12 has been deposited a set of electrodes 20. In this embodiment the electrolyte in gel form 40 is placed onto the bottom surface 14 of the substrate 10.

The electrolyte gel 40 is allowed to creep or flow through the pores 16 in the substrate 10 to the top surface 12 of the substrate 10 on which the electrodes 20 are placed. The gel 40 protrudes from this surface a sufficient amount to make contact with the electrodes 20, and provide the desired electrolytic medium. Alternately, the liquid component of the electrolyte gel is allowed to seep into the pores 16 of the substrate 10 and contact the electrodes 20. A mass of gel on the backside of the substrate 14 can serve as an electrolyte reservoir ensuring that the sensor can be maintained in an operational mode for an extended period of time. The electrodes 20 are not covered with the polymer electrolyte 40. Instead the electrolyte 40 comes through the pores 16 and is adjacent to the electrodes 20 in the region where the bottom surface 24 of the electrodes 20 contacts the top surface of the substrate 12. The electrodes 20 may also be spontaneously wetted by a thin layer (less than 0.1 micron) of the liquid component of the electrolyte gel in order to form an electrolyte layer and produce the desired "triple points".

As with the previous embodiment of the invention, the second embodiment or Everted cell has a fast response time, wherein the response time is dependent upon the species flow rate rather than its diffusion rate. The species to be detected impinges upon the sensor 2 from the front side, that is the side on which the electrodes 20 are placed. Because the species contacts the triple points 32 directly from the gaseous phase, and because the triple point area is increased, the sensor response time and sensitivity are improved.

Referring to FIG. 4, there is shown a third embodiment of a microsensor 3 of the present invention. This embodiment is substantially similar to that shown in FIG. 1, with the addition of an electrically insulating coating 50 around the surfaces of the substrate 10 which are now electrically conducting (or semiconducting). This material could be silicon, for example, and the pores fabricated from porous silicon, or by well-known silicon micromachining techniques. The insulating coating 50 covers the exposed surfaces of the substrate 10 but does not cover the passages created by the pores 16. This permits the electrolyte 30 to come in contact with the electrodes and hence to allow sensing of the species to occur.

Referring to FIG. 5, there is shown a fourth embodiment of a microsensor of the present invention. This embodiment is substantially similar to that shown in FIG. 3, with the addition of an electrically insulating coating 60 around the surfaces of the substrate 10 which are now electrically conducting (or semiconducting). This material could be silicon, for example, and the pores fabricated from porous silicon, or by well-known silicon micromachining techniques. The insulating coating 60 covers the exposed surfaces of the substrate 10 but does not cover the passages created by the pores 16. This permits the electrolyte 40 to come in contact with the electrodes and hence to allow sensing of the species to occur.

While the invention has been described with reference to the specific embodiments disclosed, it will be understood that it is capable of further modification, and this application is intended to cover any such variations, uses, or adaptations of the invention herein disclosed.

We claim:

1. A sensor for gaseous and vaporous species, comprising:
   a gas and vapor permeable substrate with a top and bottom surface, said surfaces generally facing away from one another;
   a porous electrode located on said top surface of said substrate; and
   a porous electrolyte medium in contact with said electrode and said top surface of said substrate covering only a portion of said electrode.

2. The sensor of claim 1 wherein said substrate is electrically insulating.

3. The sensor of claim 1 wherein said substrate is not electrically insulating and further comprising an electrically insulating coating on the portions of said substrate which are in contact with said electrode and electrolyte.

4. The sensor of claim 1 wherein said substrate contains pores connecting said top and bottom surfaces.

5. The sensor of claim 1 wherein said substrate is a microporous material with tortuous pore paths.

6. The sensor of claim 1 wherein said electrode is a metal.

7. The sensor of claim 1 wherein said electrode is a semiconductor material.

8. The sensor of claim 1 wherein said electrolyte is a hydrogel.

9. The sensor of claim 1 wherein said electrolyte is a polymer electrolyte.

10. A sensor for gaseous and vaporous species, comprising:
    a gas and vapor permeable substrate with a top and bottom surface, said surfaces generally facing away from one another with a plurality of pores connecting the top and bottom surfaces;
    an electrode located on said top surface of said substrate covering only a portion thereof; and
    an electrolyte medium supplied from said bottom surface of said substrate through said pores and in contact with said electrode on said top surface and covering only a portion thereof.

11. The sensor of claim 10 wherein said substrate is electrically insulating.

12. The sensor of claim 10 wherein said substrate is not electrically insulating and further comprising an electrically insulating coating on the portions of said substrate which are in contact with said electrode and electrolyte.

13. The sensor of claim 10 wherein said substrate is a microporous material with tortuous pore paths.

14. The sensor of claim 10 wherein said electrode is a metal.

15. The sensor of claim 10 wherein said electrode is a semiconductor material.

16. The sensor of claim 10 wherein said electrolyte is a hydrogel.

17. The sensor of claim 10 wherein said electrolyte is a polymer electrolyte.

18. The sensor of claim 10 wherein a reservoir of said electrolyte is in contact with said bottom surface of said substrate.

* * * * *